US011608624B2

(12) United States Patent
Hall et al.

(10) Patent No.: US 11,608,624 B2
(45) Date of Patent: Mar. 21, 2023

(54) TOILET WITH BOWL FOR SEPARATING URINE AND FECES

(71) Applicant: Hall Labs, LLC, Provo, UT (US)

(72) Inventors: David R. Hall, Provo, UT (US); David Crismon, Herriman, UT (US)

(73) Assignee: Hall Labs LLC, Provo, UT (US)

( * ) Notice: Subject to any disclaimer, the term of this patent is extended or adjusted under 35 U.S.C. 154(b) by 0 days.

(21) Appl. No.: 16/840,197

(22) Filed: Apr. 3, 2020

(65) Prior Publication Data

US 2021/0054610 A1 Feb. 25, 2021

Related U.S. Application Data

(63) Continuation-in-part of application No. 16/709,549, filed on Dec. 10, 2019, now Pat. No. 11,363,920, and a continuation-in-part of application No. 16/709,028, filed on Dec. 10, 2019, and a continuation-in-part of application No. 16/709,505, filed on Dec. 10, 2019, now Pat. No. 11,311,154, and a continuation-in-part of application No. 16/709,163, filed on Dec. 10, 2019.

(60) Provisional application No. 62/907,408, filed on Oct. 9, 2019, provisional application No. 62/907,432, filed on Sep. 27, 2019, provisional application No. 62/892,927, filed on Aug. 28, 2019, provisional application No. 62/888,663, filed on Aug. 19, 2019, (Continued)

(51) Int. Cl.
*E03D 11/02* (2006.01)
*E03D 9/00* (2006.01)
*G01N 33/493* (2006.01)
*G01N 33/483* (2006.01)
*E03D 11/13* (2006.01)
*E03D 11/11* (2006.01)

(52) U.S. Cl.
CPC .............. *E03D 11/02* (2013.01); *E03D 9/00* (2013.01); *E03D 11/11* (2013.01); *E03D 11/13* (2013.01); *G01N 33/4833* (2013.01); *G01N 33/493* (2013.01)

(58) Field of Classification Search
CPC ........ E03D 11/02; E03D 11/11; E03D 11/13; A61B 10/0038; A61B 10/007; G01N 33/4833; G01N 33/493
See application file for complete search history.

(56) References Cited

U.S. PATENT DOCUMENTS 4,052,758 A * 10/1977 Arena .................. E03D 5/014
4/320
4,197,598 A * 4/1980 Lemmon ............. E03D 1/142
4/326

(Continued)

FOREIGN PATENT DOCUMENTS

CN 106759720 A * 5/2017
CN 109667326 A * 4/2019
WO WO-2005025397 A1 * 3/2005 ............. A47K 11/02

*Primary Examiner* — Erin Deery

(57) ABSTRACT

A an analytical toilet comprising a bowl for receiving excreta comprising a platform for receiving feces; a urine drain; a feces outlet from the bowl; and a urine outlet from the bowl; wherein the platform and drain are separated by a raised hump; at least one first load cell for detecting the weight of the bowl; at least one fecal sensor for detecting at least one property of the feces; and at least one urine sensor for detecting at least one property of the urine is disclosed.

16 Claims, 17 Drawing Sheets

Related U.S. Application Data provisional application No. 62/888,683, filed on Aug. 19, 2019.

(56) References Cited

U.S. PATENT DOCUMENTS

| | | | | | |
|---|---|---|---|---|---|
| 5,073,500 | A | * | 12/1991 | Saito | A61B 5/14507 |
| | | | | | 436/53 |
| 5,149,399 | A | * | 9/1992 | Kishi | B01D 3/00 |
| | | | | | 4/111.2 |
| 2009/0288245 | A1 | * | 11/2009 | Kamiya | E03D 11/16 |
| | | | | | 4/252.1 |
| 2016/0000378 | A1 | * | 1/2016 | Hall | A61B 5/14532 |
| | | | | | 702/19 |
| 2016/0374619 | A1 | * | 12/2016 | Borkholder | A61B 5/1102 |
| | | | | | 600/301 |

* cited by examiner

TOILET WITH BOWL FOR SEPARATING URINE AND FECES

CROSS-REFERENCE TO RELATED APPLICATIONS

This application is a Continuation-in-Part of U.S. patent application Ser. No. 16/709,028 titled "Toilet with Internal Frame and Shroud" filed Dec. 10, 2019 which claims priority to 62/862,564 titled "Toilet with Frame, Bowl and Shroud" filed on Jun. 17, 2019; Ser. No. 16/709,163 titled "Toilet with Internal Lifting System" filed Dec. 10, 2019 which claims priority to 62/888,683 titled "Toilet with Multiple Point Lifting System" filed Aug. 19, 2019; Ser. No. 16/709,505 titled "Toilet with Personalized Lifting System" filed Dec. 10, 2019 which claims priority to 62/907,408 titled "Toilet with Personalized Lifting System for Bowl and Seat" filed on Oct. 9, 2019; and Ser. No. 16/709,549 titled "Toilet with User Weight-Driven Seat Lift Profile" filed Dec. 10, 2019 which claims priority to 62/907,432 titled "Toilet with User Weight Driven Seat Lift Profile" filed on Sep. 27, 2019, each of which are incorporated herein by reference in their entireties. This application also claims priority to U.S. Provisional Patent Application No. 62/888,663 titled "Toilet with Suspended Bowl to Measure Excreta Mass" filed Aug. 19, 2019; 62/862,574 titled "Toilet with Imaging Analysis of Fecal Matter" filed on Jun. 17, 2019; 62/862,577 titled "Toilet Lid for Sealing Bowl During Analysis and Washing" filed on Jun. 17, 2019; and 62/892,927 titled "Toilet with Visual Indicator of Health and Wellness Information" filed Aug. 28, 2019; each of which are incorporated herein by reference in their entireties.

TECHNICAL FIELD

The present disclosure relates to analytical toilets. More particularly, it relates to analytical toilets that separate urine and feces for analysis.

BACKGROUND

The ability to track an individual's health and wellness is currently limited to the lack of available data related to personal health. Many diagnostic tools are based on examination and testing of excreta, but the high cost of frequent doctor's visits and/or scans make these options available only on a very limited and infrequent basis. Thus, they are not widely available to people interested in tracking their own personal wellbeing.

Toilets present a fertile environment for locating a variety of useful sensors to detect, analyze, and track trends for multiple health conditions. Locating sensors in such a location allows for passive observation and tracking on a regular basis of daily visits without the necessity of visiting a medical clinic for collection of samples and data. Monitoring trends over time of health conditions supports continual wellness monitoring and maintenance rather than waiting for symptoms to appear and become severe enough to motivate a person to seek care. At that point, preventative care may be eliminated as an option leaving only more intrusive and potentially less effective curative treatments. An ounce of prevention is worth a pound of cure.

At present, there is no easy, hands-off way of measuring human waste weight, volume and density. While each can be done, there is no know automated method integrated in a toilet. Weighing an entire toilet is difficult and traditional toilets do not hold the entire urine event in the bowl, so the best that can be done is to measure the weight of a person before and after using the toilet. This could measure total excreta mass, but there would be no distinction between liquid and solid waste. Also, when you are measuring a small change in weight from a much larger weight (like the weight of waste compared to the weight of an adult) the measurement will typically be less accurate.

Just a few examples of smart toilets and other bathroom devices can be seen in the following U.S. Patents and Published Applications: U.S. Pat. No. 9,867,513, entitled "Medical Toilet With User Authentication"; U.S. Pat. No. 10,123,784, entitled "In Situ Specimen Collection Receptacle In A Toilet And Being In Communication With A Spectral Analyzer"; U.S. Pat. No. 10,273,674, entitled "Toilet Bowl For Separating Fecal Matter And Urine For Collection And Analysis"; US 2016/0000378, entitled "Human Health Property Monitoring System"; US 2018/0020984, entitled "Method Of Monitoring Health While Using A Toilet"; US 2018/0055488, entitled "Toilet Volatile Organic Compound Analysis System For Urine"; US 2018/0078191, entitled "Medical Toilet For Collecting And Analyzing Multiple Metrics"; US 2018/0140284, entitled "Medical Toilet With User Customized Health Metric Validation System"; US 2018/0165417, entitled "Bathroom Telemedicine Station"; U.S. Ser. No. 15/222,267, entitled "THIN WEIGHT SCALE." The disclosures of all these patents and applications are incorporated by reference in their entireties.

SUMMARY

In a first aspect, the disclosure provides an analytical toilet comprising a bowl for receiving excreta comprising a platform for receiving feces; a urine drain; a feces outlet from the bowl; and a urine outlet from the bowl; wherein the platform and drain are separated by a raised hump; at least one first load cell for detecting the weight of the bowl; at least one fecal sensor for detecting at least one property of the feces; and at least one urine sensor for detecting at least one property of the urine.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Figure 1:
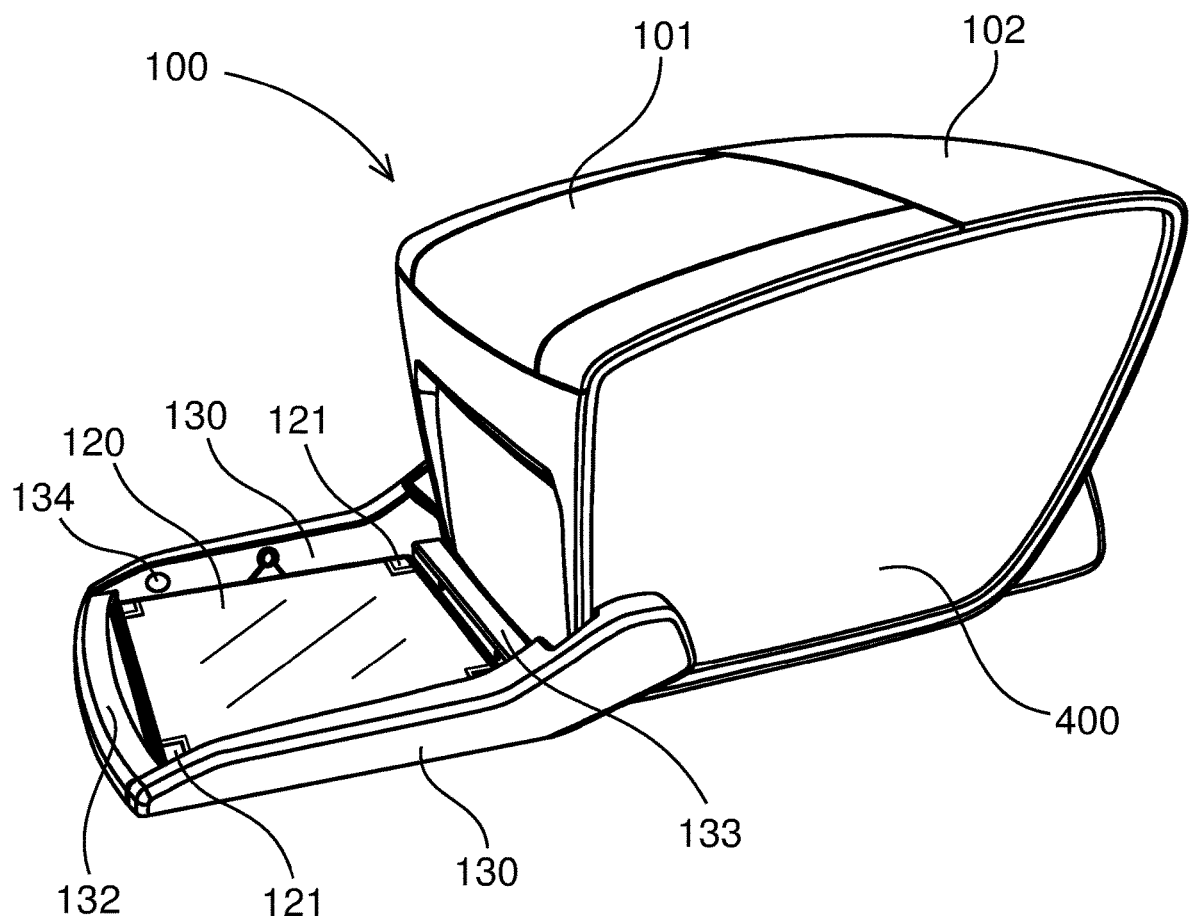
FIG. 1 is a perspective view of a first exemplary toilet according to the present disclosure in a closed position.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, the term "excreta" refers to any substance released from the body including urine, feces, menstrual discharge, and anything contained or excreted therewith.

As used herein, the term "toilet" is meant to refer to any device or system for receiving human excreta, including urinals.

As used herein, the term "bowl" is meant to refer to the portion of a toilet that is designed to receive excreta.

As used herein, the term "frame" refers to the portion of the toilet below and around the bowl supporting it, the seat, and any other toilet components.

As used herein, the term "shroud" is meant to refer to the outer surface of the toilet enclosing and covering the frame and typically other toilet components.

As used herein, the term "actuator" is intended to have a relatively broad meaning, referring to any mechanical device for moving the seat and/or bowl. Various types of actuators are suitable for use in the invention. The preferred actuators use hydraulic or pneumatic cylinders. Alternatively, the actuators use screws, levers, hydraulics, pistons, or some other mechanism to raise and lower the seat and/or bowl.

As used herein, the term "processor" is meant to refer to logic circuitry that processes data from the sensors, applies algorithms such as computer vision to identify a user or determine physical characteristics of a user, and instructs a digital controller to adjust the toilet seat and/or bowl position based on the preferences of a known user or characteristics of an unknown (i.e., unidentified) user.

As used herein, the term "position," as in the position of the bowl, seat or footrest, is intended to refer to the height and/or the angle of the device, with respect to the floor.

As used herein, the term "angle," as in angle of the seat, is intended to refer to the angle of the seat versus the horizontal floor (i.e., 0° angle) so that increasing the angle refers to the seat approaching perpendicular (i.e., 90° angle).

As used herein, the term "weight" is meant to refer to the mass of a user or their excreta.

As used herein, the term "floating" refers to a component that is supported by weight sensors independently of other components and does not support other components (e.g., a floating bowl does not support the weight of the seat).

As used herein, the term "removable" refers to any portion of the shroud that can be moved to allow access to the interior components of the toilet whether such portion is detached from the toilet or merely moved (e.g., slid over or pivoted on at least one hinges) to provide access.

As used herein, the term "sensor" is meant to refer to any device for detecting and/or measuring a property of a person or of a substance regardless of how that property is detected or measured, including the absence of a target molecule or characteristic.

As used herein, the term "imaging sensor" is meant to refer to any device for detecting and/or measuring a property of a person or of a substance that relies on electromagnetic radiation of any wavelength (e.g., visible light, infrared light, xray) or sound waves (e.g., ultrasound) to view the surface or interior of a user or substance. The term "imaging sensor" does not require that an image or picture is created or stored even if the sensor is capable of creating an image.

As used herein, the terms "weight sensor" and "load cell" are intended to have a relatively broad meaning, referring to a transducer, specifically a force transducer that converts a force such as tension, compression, pressure, or torque into an electrical signal that can be measured and standardized. As the force applied to the weight sensor or load cell increases, the electrical signal changes proportionally.

As used herein, the term "excretion profile" is meant to refer collectively to the rate of excretion at any moment in time of an excretion event and the total volume or mass of excreta as a function of time during an excretion event. The terms "defecation profile" and "urination profile" refer more specifically to the separate measurement of excreta from the anus and urethra, respectively.

As used herein, the term "consistency" is meant to refer to properties of excreta, particularly fecal matter and anything in fecal matter, related to solidity, liquidity, and hardness.

Exemplary Embodiments

The present disclosure relates to a toilet with a bowl and seat supported by a frame. The frame includes at least one lifting mechanism adapted to raise and lower the seat and/or bowl. In some embodiments, there may be separate frames for supporting and adjusting the seat and for supporting and adjusting the bowl. Preferably, the lifting mechanism is further adapted to change the angle of the seat.

In a preferred embodiment, the toilet comprises a motorized seat lift that is integral with and internal to the toilet. It also provides customized lifting motions set to individual user's preferences. The disclosed toilet looks and feels like a conventional toilet and can help prevent fall by keeping a person more supported during a lift and help them to their feet at a height appropriate for the individual.

In a preferred embodiment, the adjustable frame allows the toilet to be both shorter and taller than conventional toilets. This makes the toilet more comfortable and easier to use for both tall and short users, including children, without the need for special stools or spacers.

In various exemplary embodiments, the bowl is supported by a frame including at least one actuator. In various exemplary embodiments, the seat is supported a frame comprising at least one actuator. In various exemplary embodiments, the frame comprises two, three, four, or more actuators for the bowl and/or seat. In a more preferred embodiment, the frame comprises three pairs of actuators to move the seat. Preferably, the actuators are controlled by a digital controller that coordinates the actions of the actuators to thereby provide a smooth lifting and lower at the desired speed. More preferably, the controller is programmable, so that users can program the lifting and lowering of the seat to their preference. Even more preferably, the toilet includes a user identification module, so that the user is automatically identified as he or she approaches or sits on the toilet.

Figure 2:
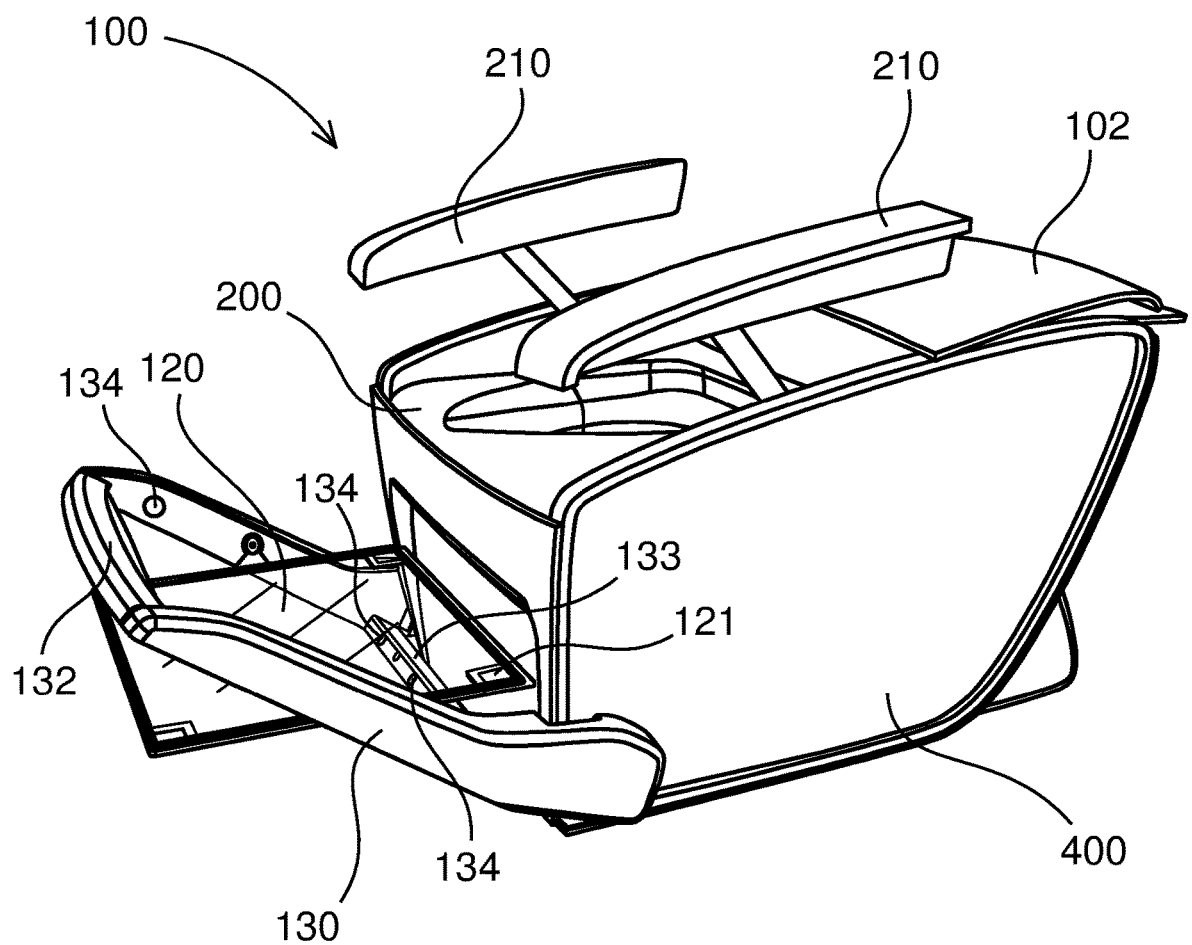
FIG. 2 is a perspective view of the toilet of FIG. 1 with the lid opened and an exemplary embodiment of handles deployed.

Referring to FIG. 1, an exemplary embodiment of a toilet is shown with a closed lid 101, lowered foot platform 120, and retracted handles 210. FIG. 2 shows the toilet with an open lid 101, raised foot platform 120, and extended handles 210. In a preferred embodiment, handles 210 are adapted to be readily ripped by a user, especially while sitting or rising. In a preferred embodiment, the handles 210 move while the seat 200 is lowering and lifting a user to enable them to grip the handles 210 and use them for support during sitting and rising. The toilet is enclosed with a shroud 400.

In various exemplary embodiments, the shroud 400 covers all the internal support components that comprise the frame as well as the bowl 300 (i.e., the bowl is covered except for the top that would be covered by a lid). In preferred embodiments, the shroud 400 comprises at least one sections of articulated or flexible (e.g., elastic, material) assembled such that the shroud 400 can contract or expand as the frame 110 moves the bowl 300 and/or seat 200. Other sections of the shroud may be rigid. In various exemplary embodiments, the at least some portions of the shroud are removable or openable to allow access to the interior of the toilet frame. The interior of the toilet frame may include, among other things, plumbing connections, fluid supply lines, support structures, health and wellness assessment devices, electronic circuits, digital devices (e.g., processors, memory), storage tanks, and communication modules. In various preferred embodiments, cover 102 opens to allow access to the interior of the frame.

In various exemplary embodiments, the shrouds 400 are preferably designed for aesthetic and other purposes. For example, the shrouds 400 can be made in various colors to suit the décor of the bathroom the toilet is installed in. Besides colors, the shrouds 400 can include patterns or graphics so that the toilet 100 "makes a statement" in the bathroom.

In various exemplary embodiments, the handles 210 include at least one buttons, switches, sensors, etc. through which the user may control the seat, including, but not limited to, starting and stopping the seat 200, reversing seat movement direction, adjusting the position or angle of the seat 200, and adjusting the height of the bowl 300, seat 200, or foot platform 120.

In various exemplary embodiments, the handles 210 may include at least one health and wellness sensors. The sensors may be used to measure how hard the user is gripping and provide feedback to the lift control. For example, if a user suddenly increases their grip it is likely that they are struggling with standing or with their balance. Grip pressure may also be tracked over time. The sensors may also include detection for heart rate, body temperature, hand health indicators, light sensors, electrocardiogram, pulse, blood test (e.g., using a finger prick), etc. Toilet handles with health and wellness sensors are disclosed in U.S. Patent Pub. No. 2018/0084959, the entire disclosure of which is incorporated herein by reference in its entirety.

Figure 3:
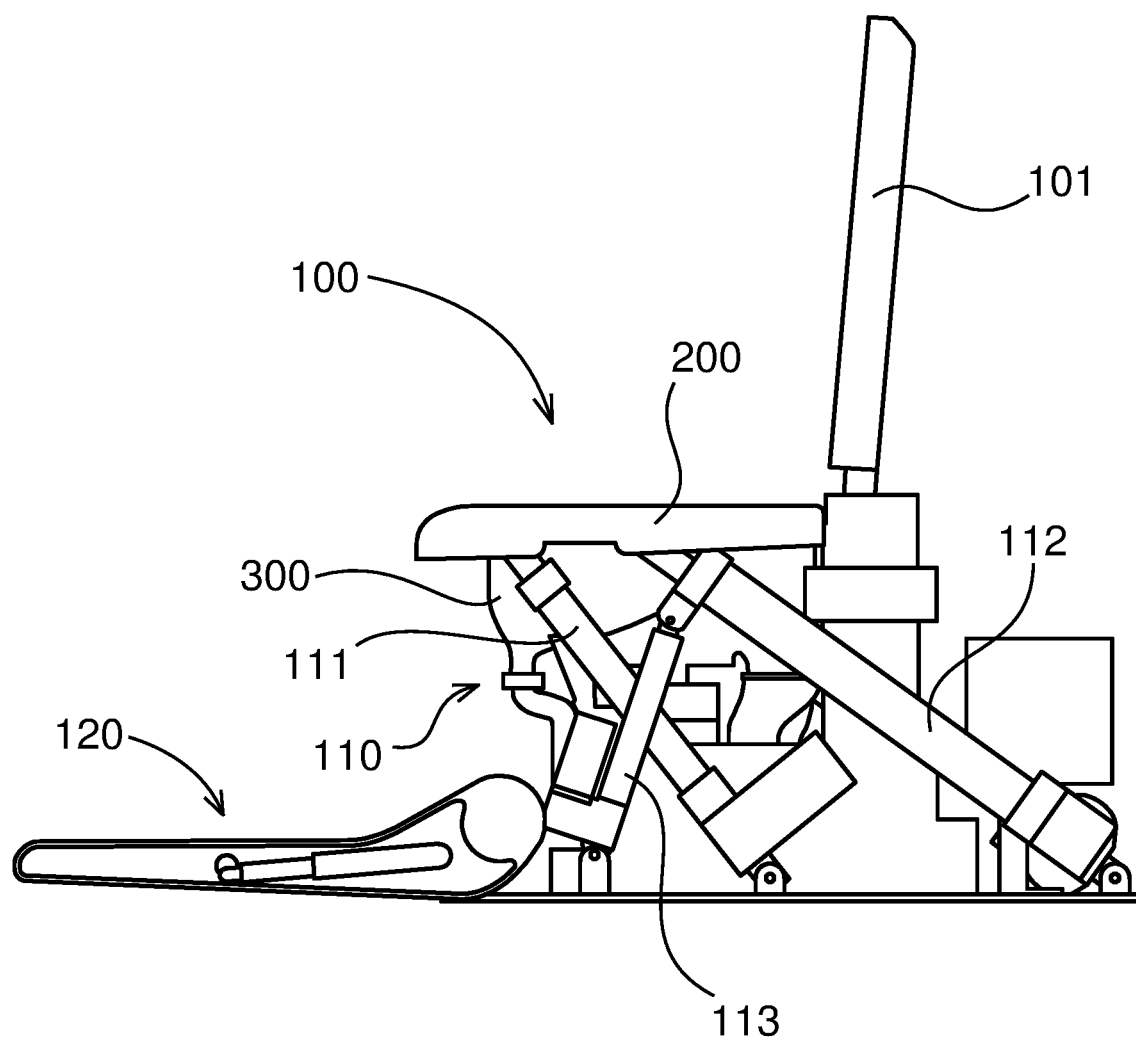
FIG. 3 is a side plan view of a second exemplary toilet according to the present disclosure with the shroud removed and the seat in a lowered position for sitting.
Figure 4:
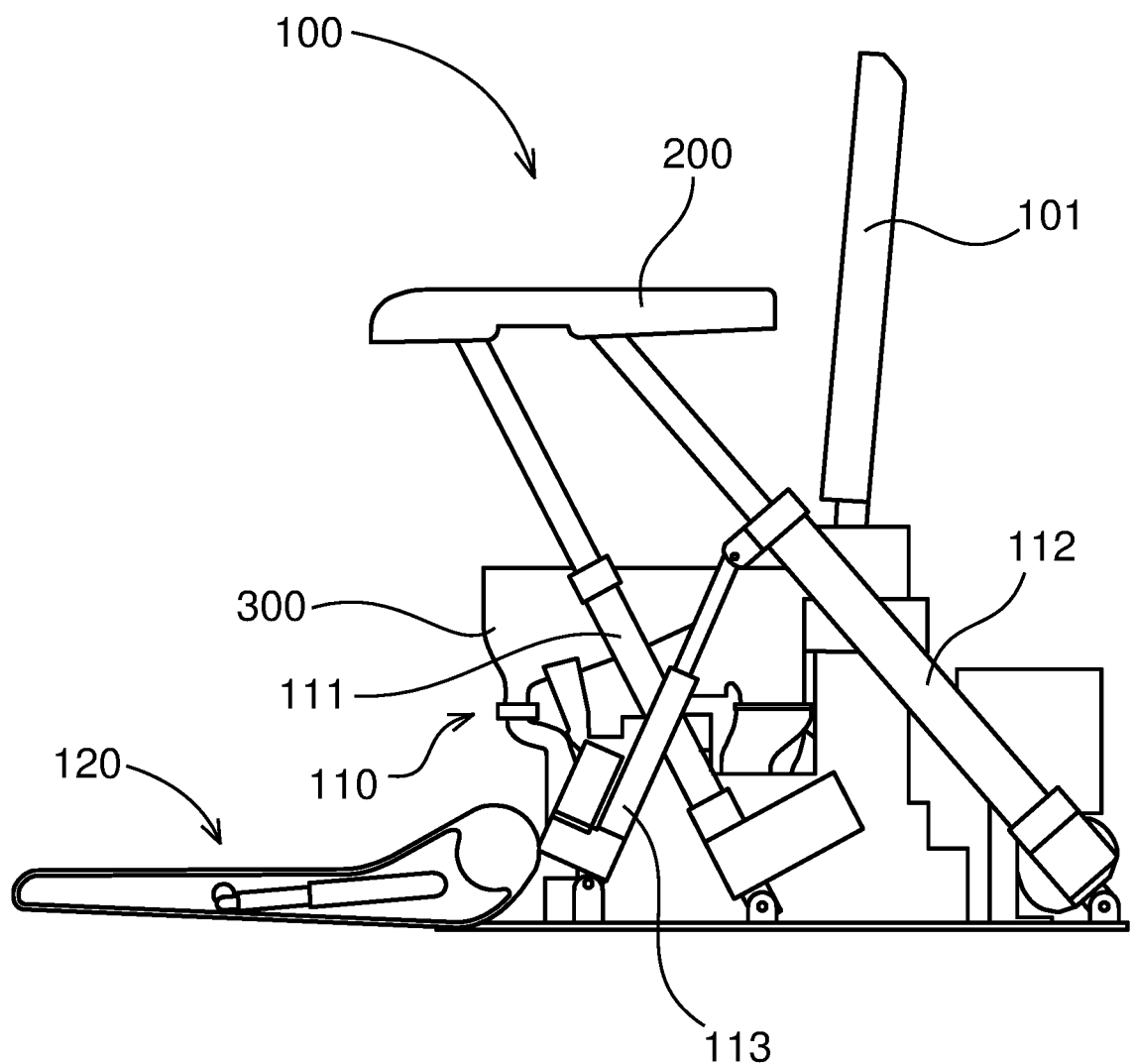
FIG. 4 is a side plan view of the toilet of FIG. 3 with the seat raised to a higher sitting position.

Referring to FIGS. 3 and 4, an exemplary embodiment of a toilet 100 is shown with various seat elevations. The toilet 100 includes a frame 110, bowl 300 supported by the frame 110, a lid 101, and a seat 200 also supported by the frame 110. In a preferred embodiment, the seat 200 is supported by two sets of seat actuators 111, 112, and 113. In other embodiments, the number and arrangement of actuators may vary.

In a preferred embodiment, a pair of first seat actuators 111 are pivotally connected to a front area of the seat 200 and a pair of second seat actuators 112 are pivotally connected to a back area of the seat 200 providing support at four "corners" of the seat 200. The four seat actuators 111 and 112 are also pivotally attached to the frame 110. An additional pair of third seat actuators 113 are pivotally attached to the frame 110 at one end and pivotally attached to the second pair of seat actuators 112 at their other end. In another embodiment, the third seat actuators 113 are attached to the first pair of seat actuators 111.

FIG. 3 shows the toilet 100 with the seat 200 fully lowered to just above the top of the bowl 300. FIG. 4 shows the seat 200 adjusted to a greater height. This allows the seat to be adjusted for a variety of users from small children to tall adults.

Figure 5:
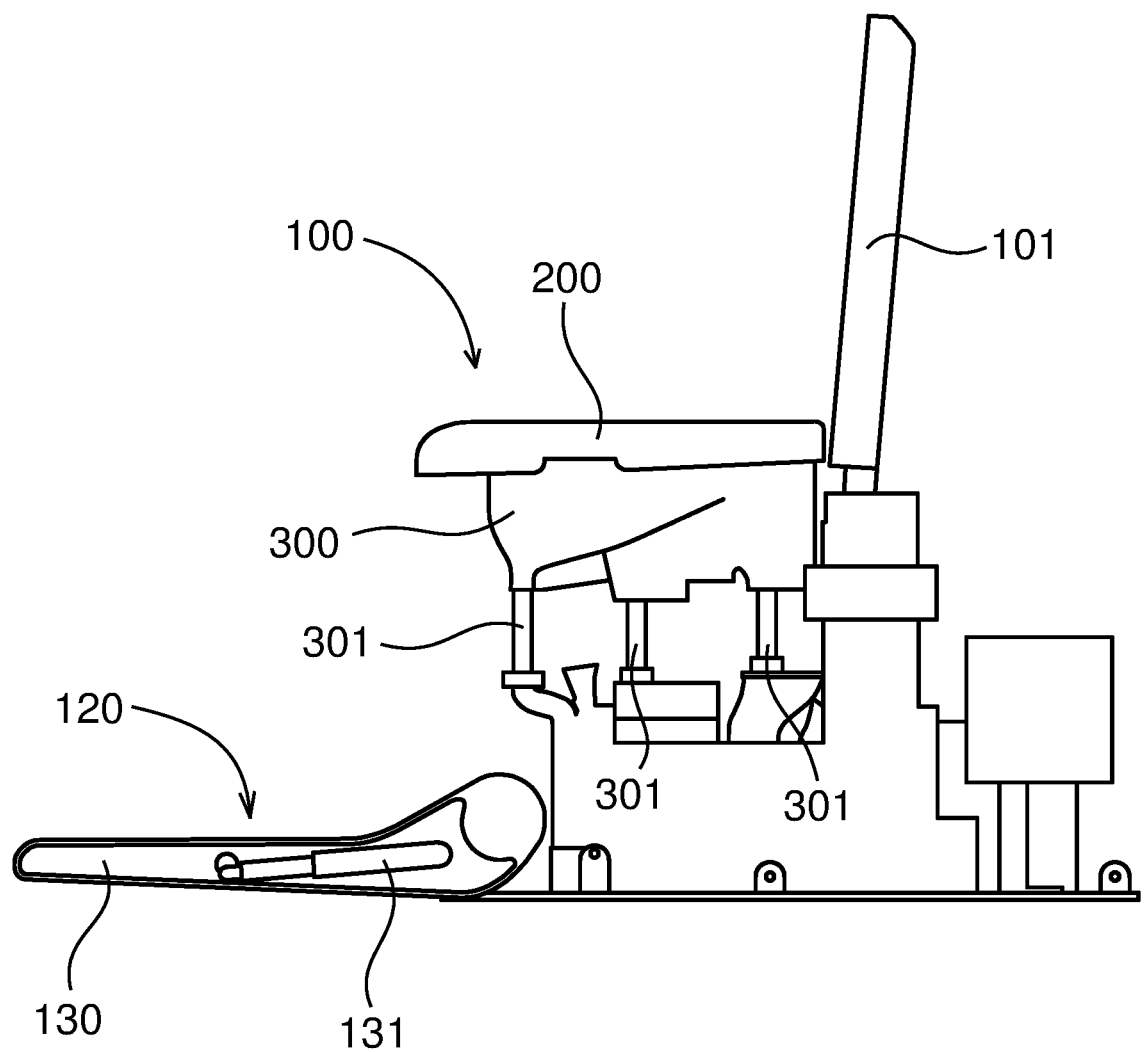
FIG. 5 is a side plan view of the toilet of FIG. 3 with the bowl raised (seat lifting actuators removed for better viewing).

Referring to FIG. 5, a bowl lift mechanism is used to elevate the bowl that includes at least one bowl actuator 301. In preferred embodiments, the shroud 400 adapts to changes to the position of the bowl. In such an embodiment, the bowl may remain in fluid connection with the drain or may be closed off until it is lowered again. In some embodiments, the toilet may be lowered into the floor to create more space for the toilet's internal components. In preferred embodiments, the shroud 400 is made from an elastic material that stretches and contracts back into its original shape.

Figure 6:
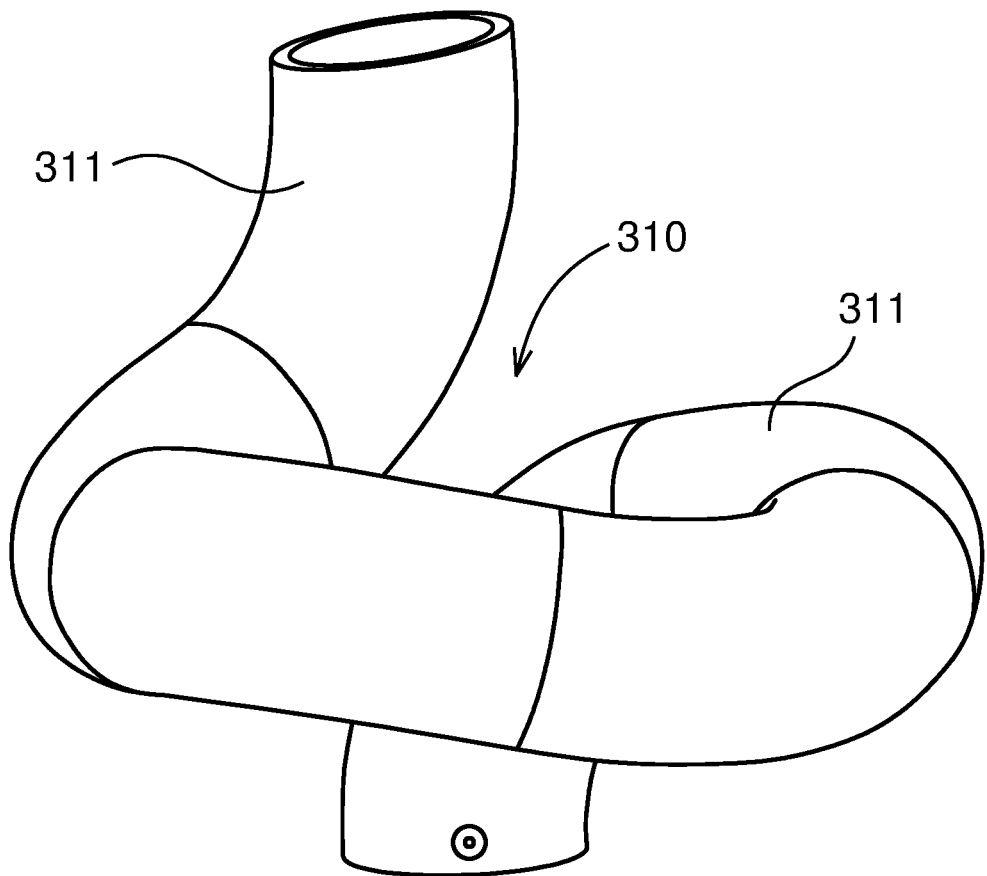
FIG. 6 is a perspective view of an exemplary embodiment of an adjustable piping system according to the present disclosure in a lowered or compacted position.
Figure 7:
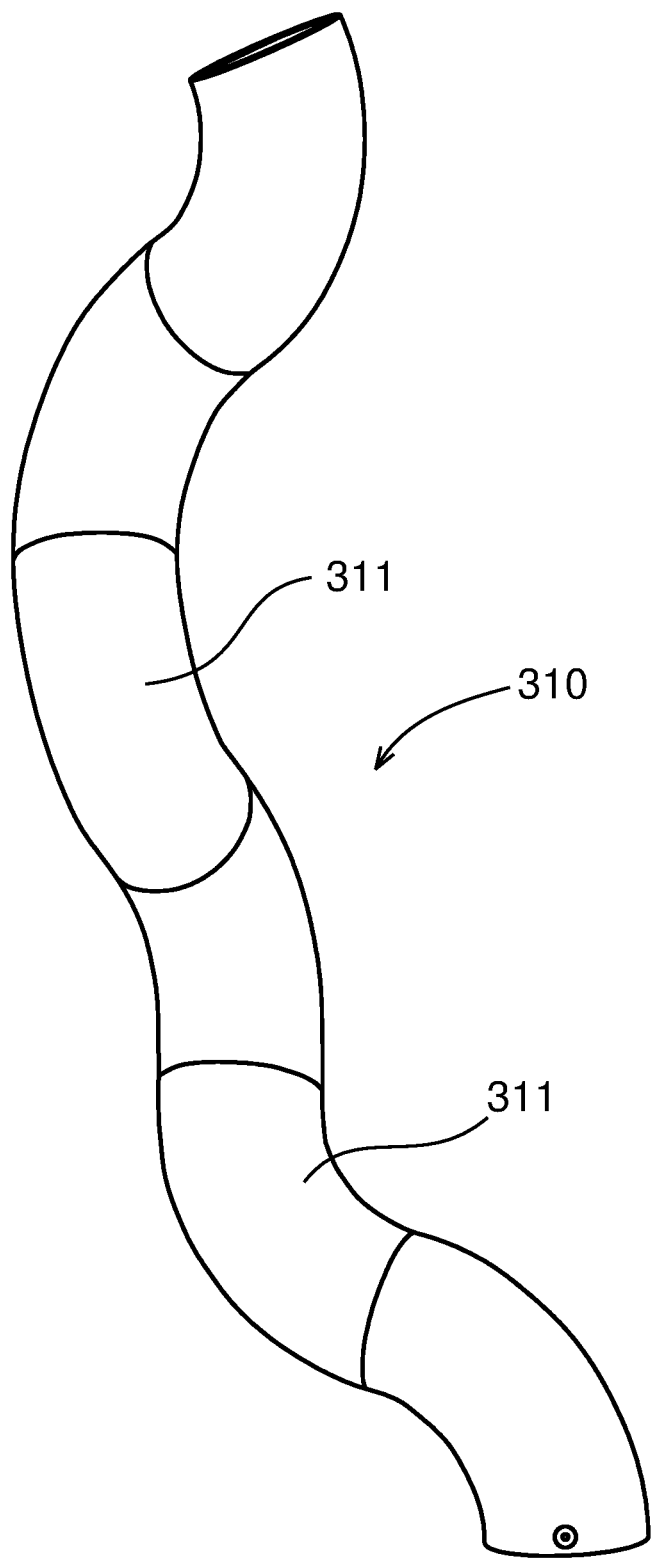
FIG. 7 is a perspective view of the piping of FIG. 6 in an extended or raised.

Referring to FIG. 6, an exemplary embodiment of a flexible tube 310 is illustrated in a lowered position. It is made of a series of rotatably connected "macaroni" shaped tubes 311. FIG. 7 shows the same tubing 310 in a raised position. The act of raising and lowering the bowl 300 with the plumbing attached could act as the flushing action. When the bowl 300 is lifted the tube 310 is straighter and empties everything into the sewer. When it lowers, it creates the standard p-trap with excess tube. The sections of tube 311 shaped like the "macaroni" could also be motorized at the joints and comprise at least part of the bowl lift mechanism.

Figure 8A:
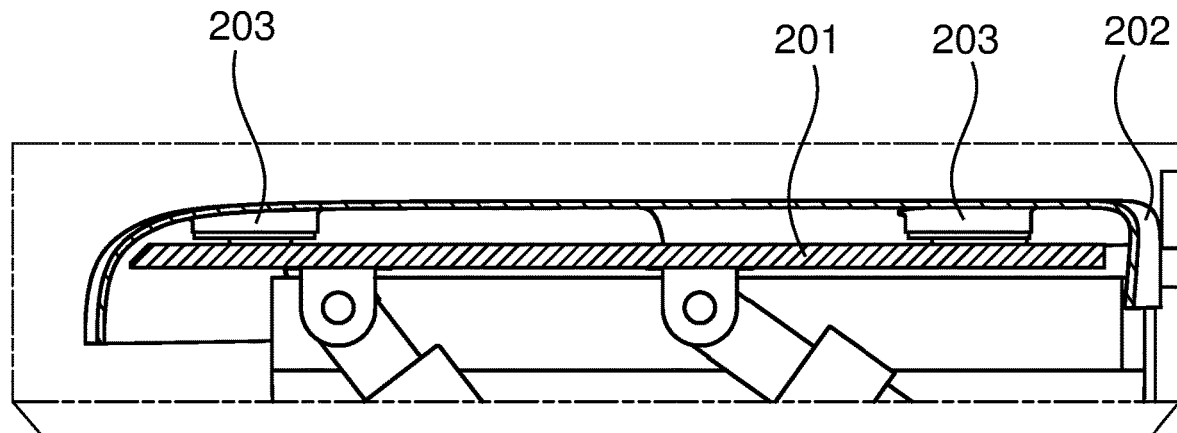
FIG. 8A is close-up view of the seat as shown in FIG. 8.
Figure 8:
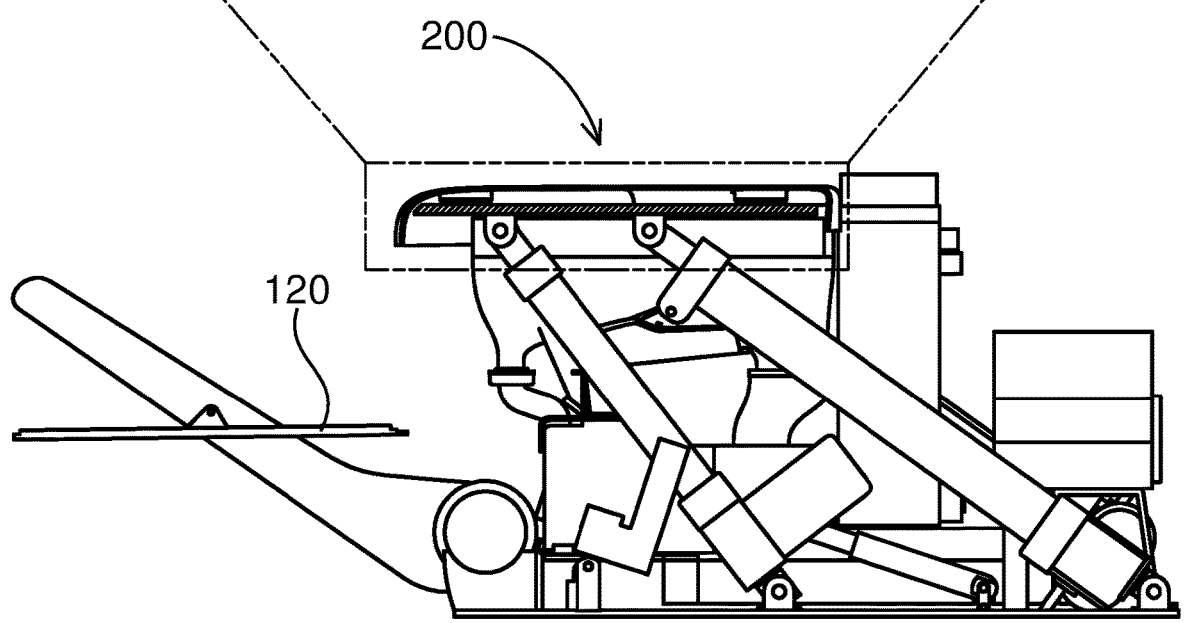
FIG. 8 is a side cross-sectional view of the toilet of FIG. 1.

Referring to FIGS. 8 and 8A, an exemplary embodiment of a floating toilet seat 200 according to the present disclosure is shown. The seat includes a rigid seat support 201 covered by a shroud 202. Weight sensors 203 are placed between the seat support 201 and floating cover 202. In various other embodiments, the weight sensors may be placed in a variety of places such as under the actuators or under the frame.

In various exemplary embodiments, the toilet continuously measures weight load on both the seat 200 and the foot platform 120. In a preferred embodiment, the system weighs the user on the foot platform 120 prior to the user placing any weight against the seat 200 and records that as the user's total weight. In some embodiments, the system calculates a user total weight using both the seat weight sensors 203 and foot platform weight sensors 121 after the user seated with the seat 200 fully lowered. In various exemplary embodiments, the system calculates the percentage of user body weight on the foot platform 120. The angle of the seat 200 is limited from raising based on the percentage of weight on the foot platform 120. This prevents the seat 200 from tipping to an angle that will not support the user's weight prior to the user being on their feet.

Figure 9:
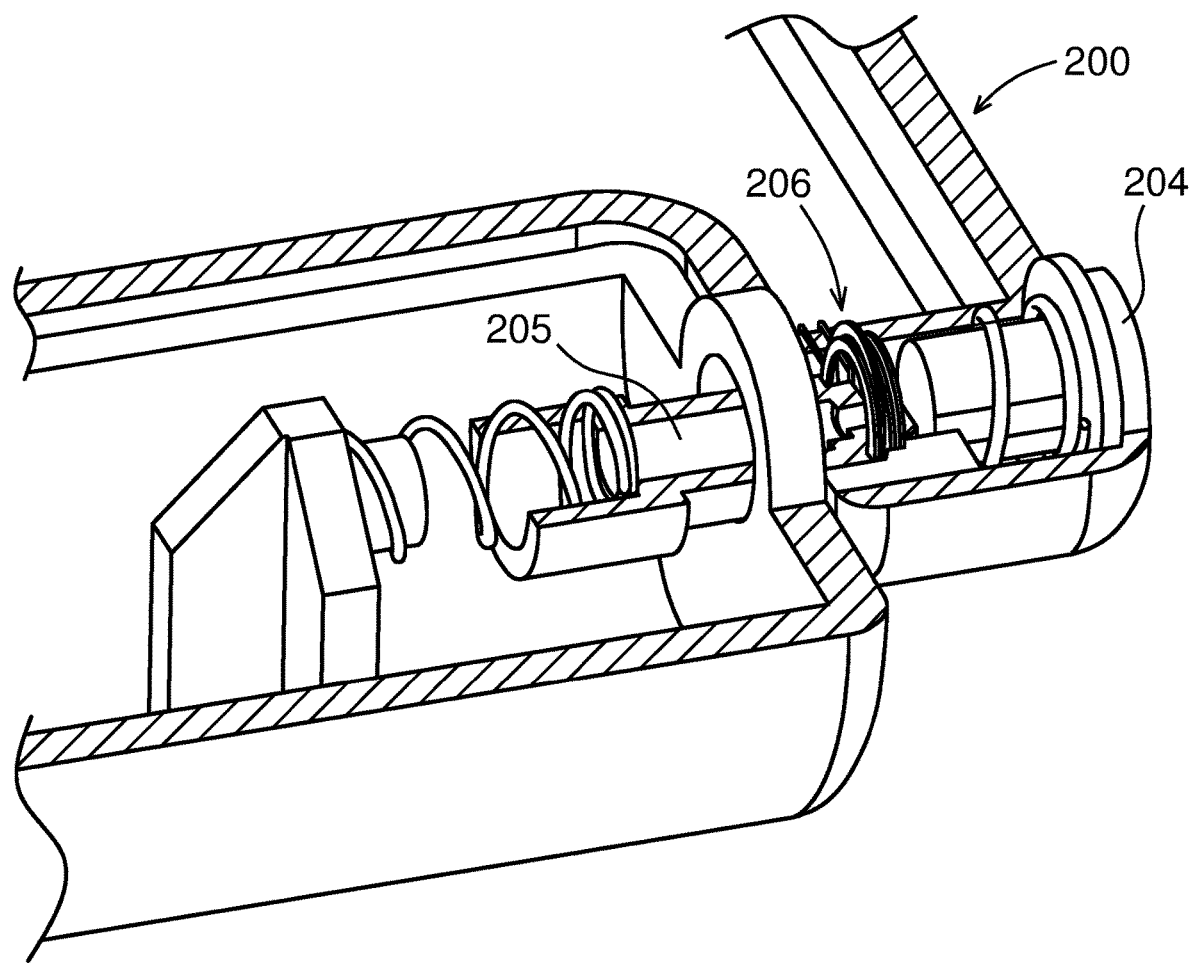
FIG. 9 is a partial perspective view of a powered quick disconnect for a toilet seat according to the present disclosure.

In accordance with the present disclosure, a design for a seat 200 that can be easily added/removed from a toilet, seat topper, seat lifter, etc. is provided. This allows for easier installation of a new seat 200 to accommodate upgraded seats and/or seat sensors. Referring to FIG. 9, a powered quick disconnect mechanism is shown. The seat 200 is removed by pressing in on the spring-loaded button 204. This moves the spring-loaded axle 205 out of the seat to allow the seat 200 to be removed. The electrical connector 206 automatically connects and disconnects with physical connection. The electrical connector 206 comprises a ring connector that maintains electrical connection throughout the seat's range of motion. This provides for electrical power and/or data connections to sensors in the seat.

Figure 10:
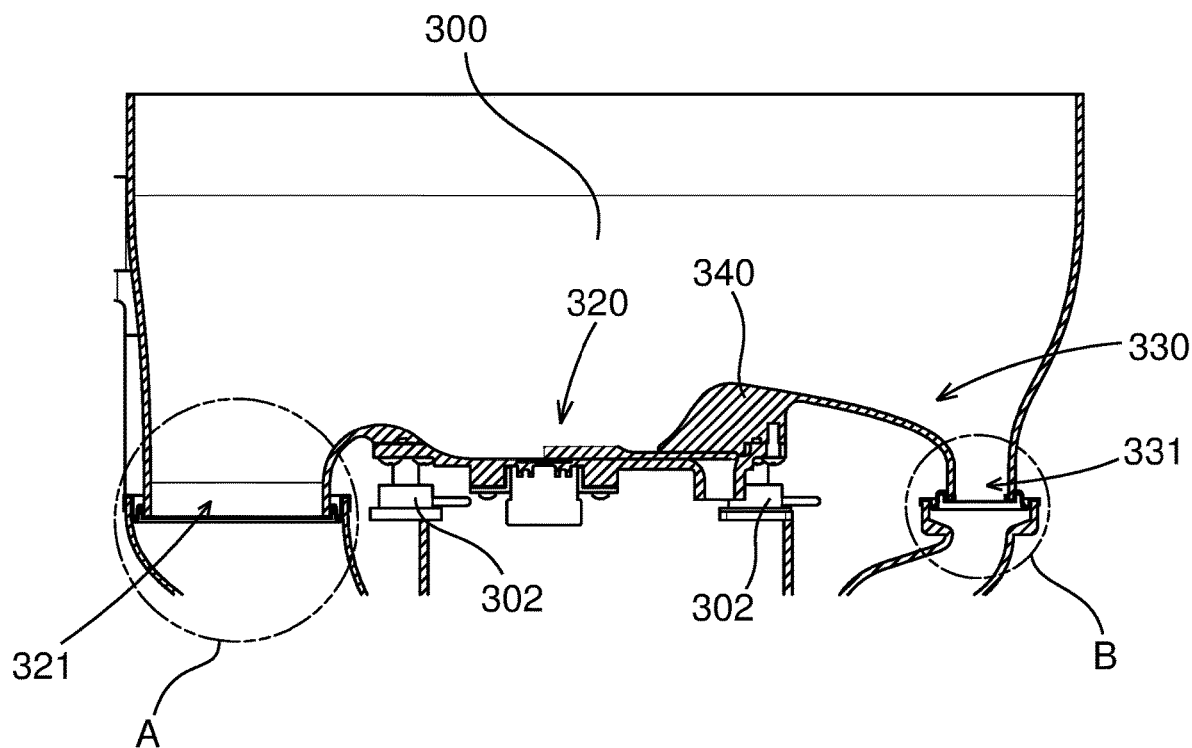
FIG. 10 is a side cross-sectional view of an exemplary embodiment of a floating bowl toilet according to the present disclosure.

Referring to FIG. 10, an exemplary embodiment of a toilet with a bowl 300 that floats on weight sensors 302 is shown. This design enables weighing excreta in the bowl 300. In such embodiments, the bowl 300 does not support the seat 200, lid 101, or any other components of the toilet 100. In various preferred embodiments, the weight sensors 302 are located between the bowl actuators 301 (see FIG. 5) and the bowl 300 but may be located anywhere in the bowl support system (e.g., under the bowl actuators 301). Once a user sits down and urinates and defecates, both are captured separately. The urine flows to its own receptacle, and the fecal matter sits on a shelf. The weight of the separated waste can be measured separately or together. If the weight is measured together, by measuring the volume of the urine, and assuming its density is equal to that of water, you can calculate the portion of the total weight that the urine is responsible for and thus calculate the weight of the fecal matter (all the remaining additional weight). With an additional sensor to estimate the size of the fecal matter, fecal density could be estimated.

In this embodiment, the bowl 300 has two first outlets 305 and 306. Outlet 305 is adapted to receive feces. Outlet 306 is adapted to receive urine. Isolating and separating feces and urine facilitates preparing samples for analysis. Valves may be used to prevent exit of excreta prior to weighing. Other embodiments may contain more or fewer outlets. In various exemplary embodiments, any type of weight sensor 302, such as pressure sensors and load cells, may be used to measure bowl weight.

In various exemplary embodiments, the bowl 300 has at least one outlet and each outlet is connected separately or together to a sewer line. The toilet 100 is connected to the sewer line using a seal that does not transfer any of the weight to the sewer line (e.g., a wiper seal).

Figure 11A:
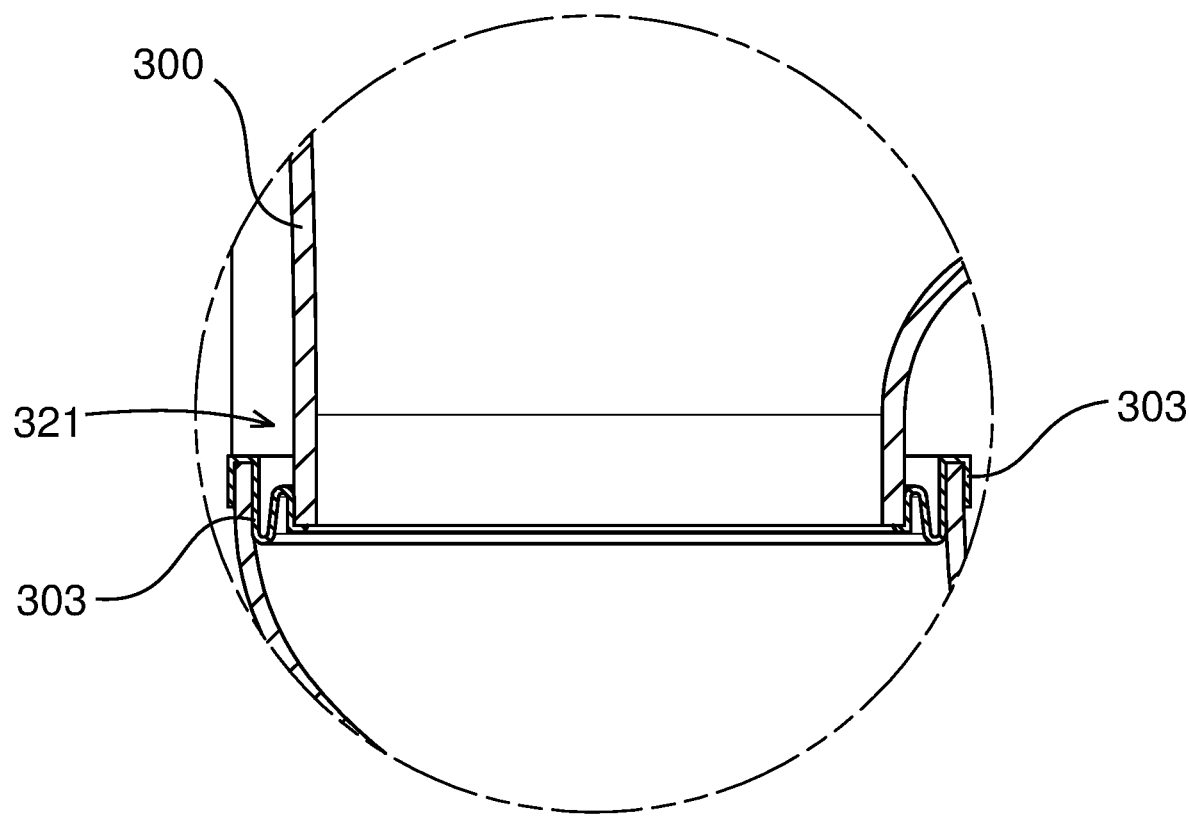
FIG. 11A is side cross-sectional view of the portion of the embodiment of FIG. 10 marked A in FIG. 10.

Referring to FIG. 11A, a first exemplary embodiments of a mechanism for sealing the connection between the floating bowl and plumbing drain is shown. A first exemplary embodiment of an annular S-seal 303 maintains a gas-tight seal between a bowl outlet and the sewage system without providing any support for the weight of the seat.

Figure 11B:
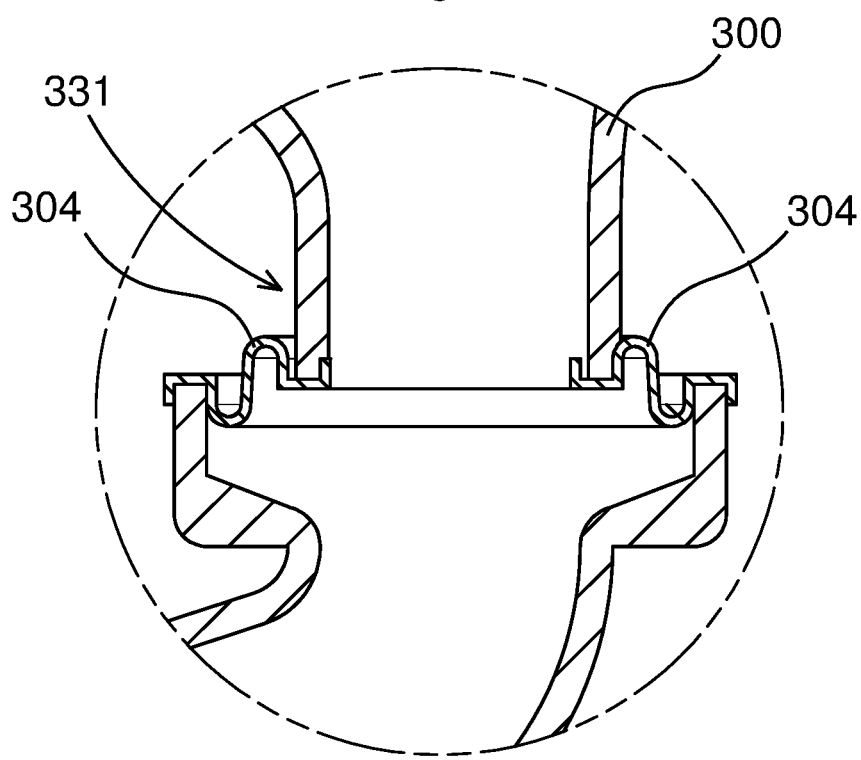
FIG. 11B is side cross-sectional view of the portion of the embodiment of FIG. 10 marked B in FIG. 10.
Figures 12A, 12B, 12C:
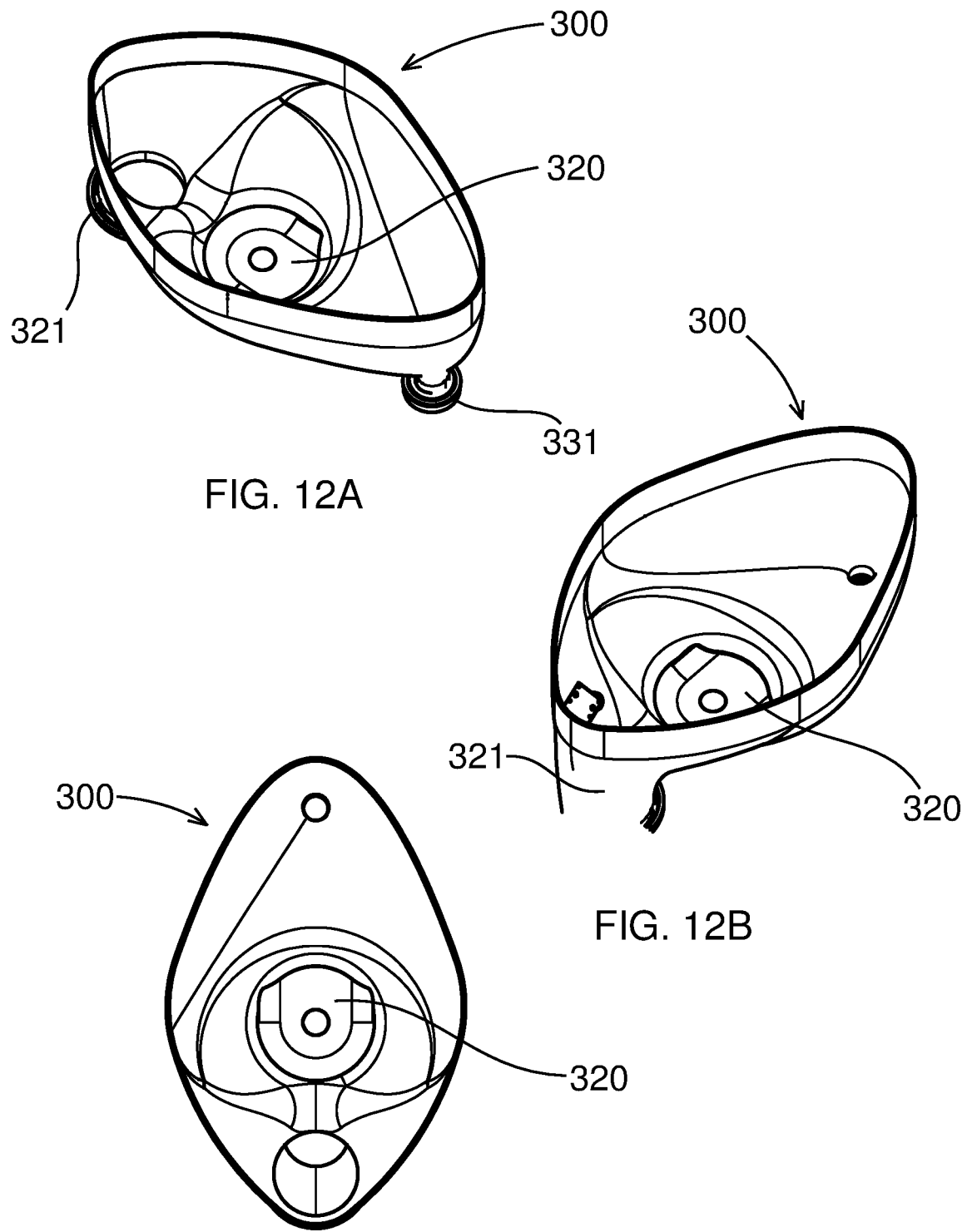
FIG. 12A is a first perspective view of the embodiment of FIG. 10.
FIG. 12B is a second perspective view of the embodiment of FIG. 10.
FIG. 12C is a top view of the embodiment of FIG. 10.
Figure 13:
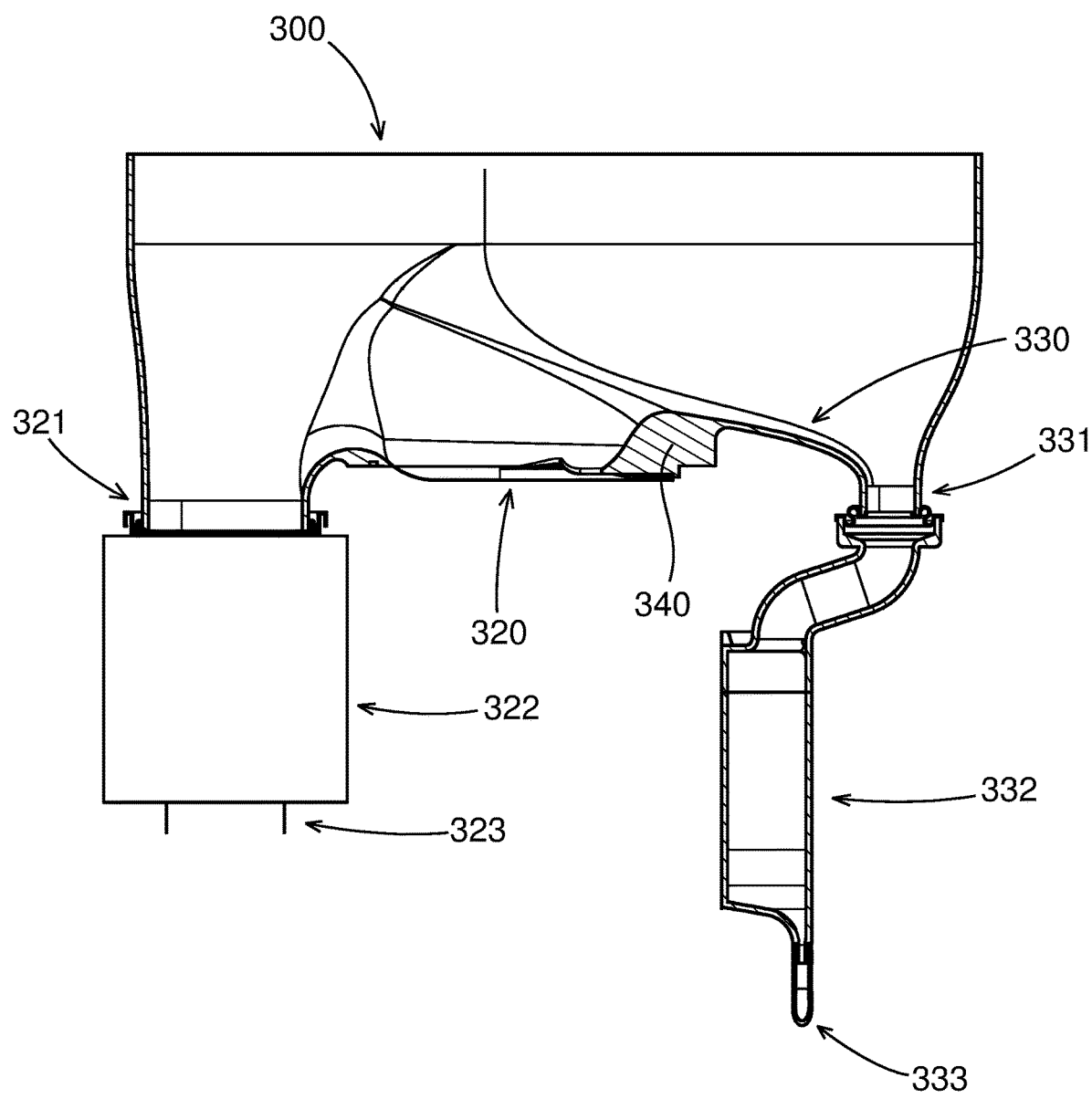
FIG. 13 is a side plan cross-sectional view of the embodiment of FIG. 10.

Referring to FIG. 11B, a first exemplary embodiments of a mechanism for sealing the connection between the floating bowl and plumbing drain is shown. A second exemplary embodiment of an annular S-seal 304 maintains a gas-tight seal between a bowl outlet and the sewage system without providing any support for the weight of the seat, i.e. without interfering with weight measure through the bowl weight sensor. In various other exemplary embodiments, other non-weight bearing sealing mechanisms such as wiper seals or other sliding seals may be used. In various exemplary embodiments, excreta are retained in the system by valves in the outlets.

Referring to FIGS. 12A, 12B, 12C, and 13 an exemplary embodiment of a bowl 300 adapted to separately collect feces and urine is shown. The bowl 300 comprises a feces collecting portion 320 and a urine collecting portion 330 separated by a raised hump 340. As discussed in more detail below, various scans or tests may be performed on the feces on the portion 320. In various exemplary embodiments, the bowl 300 includes one or more water jets to push feces off the portion 320 into feces outlet 321. In various preferred exemplary embodiments, the fecal portion 320 includes a flat horizontal platform. However, in other embodiments, the fecal portion 320 may be flat or curved (convex or concave) and may be horizontal or slanted.

In various exemplary embodiments, the first feces outlet 321 is in fluid communication with a feces receptacle 322. In various exemplary embodiments, the feces receptacle 322 retains the feces for further sampling, preparation, and/or testing prior to disposal of the feces through a second feces outlet 323. Samples may be extracted from unprocessed feces or the feces may be comminuted prior to sample extraction. Testing may be performed in the feces receptacle 322 or elsewhere. In various exemplary embodiments, the feces receptacle 320 is supported by load cells such that the mass of the feces in the receptacle may be measured. In various exemplary embodiments, scans or tests are performed on the feces on the platform 320 and/or in the receptacle 322 to determine one or more properties of the feces including weight, color, consistency, volume, density, content, temperature, pH, size and shape, excretion profile, sounds, and gas or fumes.

In various exemplary embodiments, a known quantity of liquid may be added to the fecal receptacle 320 such that the feces are submerged. The total volume of feces and liquid is measured to determine the volume of feces (total volume minus added liquid volume) which is then used to determine fecal density.

In various exemplary embodiments, the first urine outlet 331 is in fluid communication with a urine receptacle 332. In some embodiments, the urine is retained in the bowl for initial testing and released into the receptacle by a valve (not shown) for additional testing.

In various exemplary embodiments, the receptacle 332 is large in its vertical dimension relative to horizontal dimensions in order to facilitate gravimetric settling of the urine. In various exemplary embodiments, the urine receptacle 332 retains the urine for further sampling, preparation, and/or testing prior to disposal of the urine through a second urine outlet 333. Samples may be extracted from unprocessed urine shortly after urination or after the urine has been allowed to sit and gravimetrically settle. Testing may be performed in the urine receptacle 322 or elsewhere. Samples may be extracted from the urine receptacle 322 at various locations (e.g., from the bottom, top, or between) after gravimetric settling has occurred.

In various exemplary embodiments, the urine is tested for a variety of properties including volume, flow rate, color, weight, density, content, temperature, clarity, pH, settled gradient, and flow geometry. This may be done with a variety of sensors or testing methods including MOS, CCD, spectrometers, volume measurement devices, weight sensors, temperature gauges, chromatographs, mass spectrometers, and gas analyzers.

Figure 14:
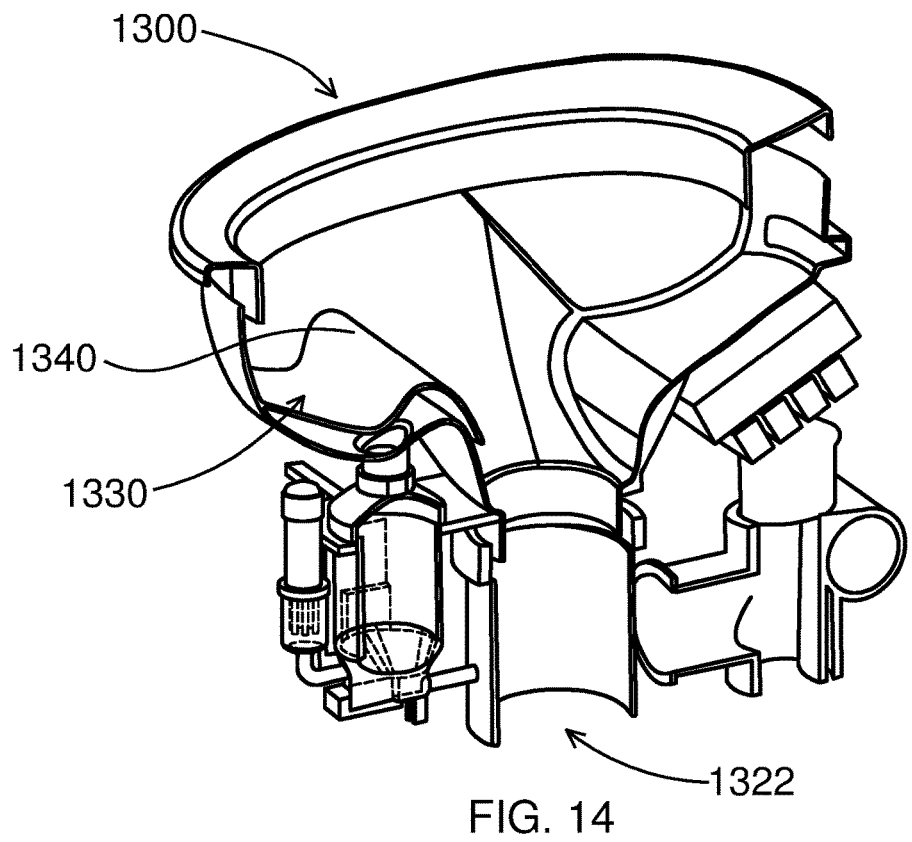
FIG. 14 is side perspective cross-sectional view of another exemplary embodiment of a toilet bowl according to the present disclosure.

Referring to FIG. 14, an alternative embodiment of a toilet bowl 1300 adapted to separately collect urine and feces is shown. The bowl 1300 includes a feces receptacle 1322 and urine drainage 1330 separated by a hump 1340. In various exemplary embodiments, as discussed above, the bowl is supported by one or more load cells allowing for weighing excreta in the bowl. In the embodiment of FIG. 14, the feces receptacle 1322 is supported by load cells separately from the bowl 1300 allowing for separate weighing of feces and urine.

Figure 15:
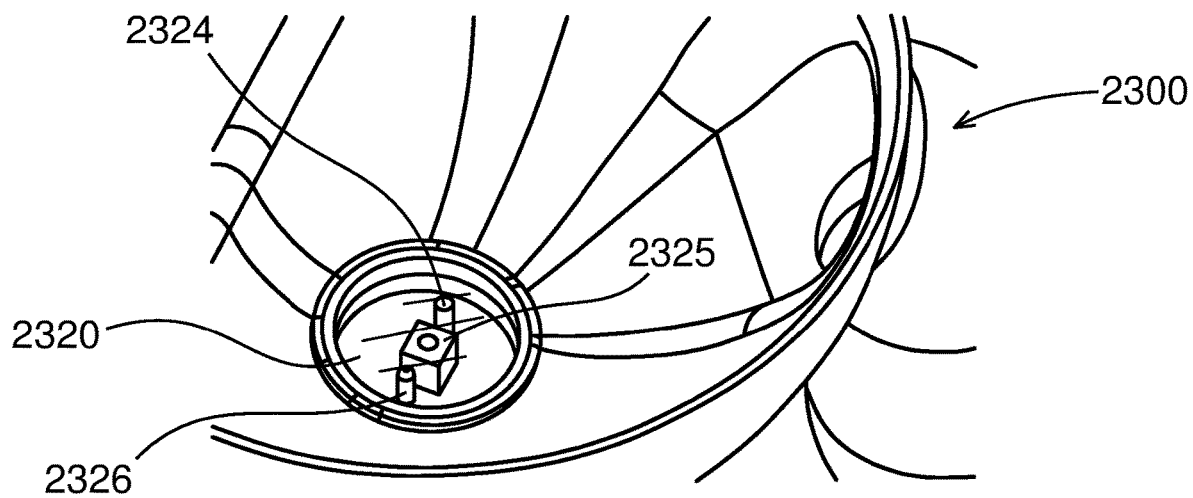
FIG. 15 is a partial top perspective view of another exemplary embodiment of a toilet bowl with a fecal platform according to the present disclosure.

Referring to FIG. 15, shows an exemplary embodiment of a feces platform 2320 for use in the bowl 2300 of an analytical toilet. In this embodiment, at least a portion of the platform 2320 is transparent. One or more sensors 2324, imaging sensors 2325, or light sources 2326. In various exemplary embodiments, the one or more imaging sensor 2325 is one or more of, but not limited to, CCD (charge-coupled device) or MOS (metal oxide semiconductor), including CMOS (complementary metal oxide semiconductor), IR (infrared) detector, near IR detector, and visible light detectors. In various exemplary embodiments, the light source 2326 emits visible and/or non-visible light across one or more ranges of wavelengths as appropriate for any particular detection method (e.g., spectrometry). In various exemplary embodiments, the sensor 2324 is one or more of, but not limited to, CCD, MOS/CMOS, spectrometers, chromatographs, FET, nanoFET, MOSFET, mass spectrometers, electrodes, microphones, load cells, pressure gauges, PPG, thermometers (including IR and thermocouples), rheometers, durometers, pH detectors, and scent detectors.

Figure 16:
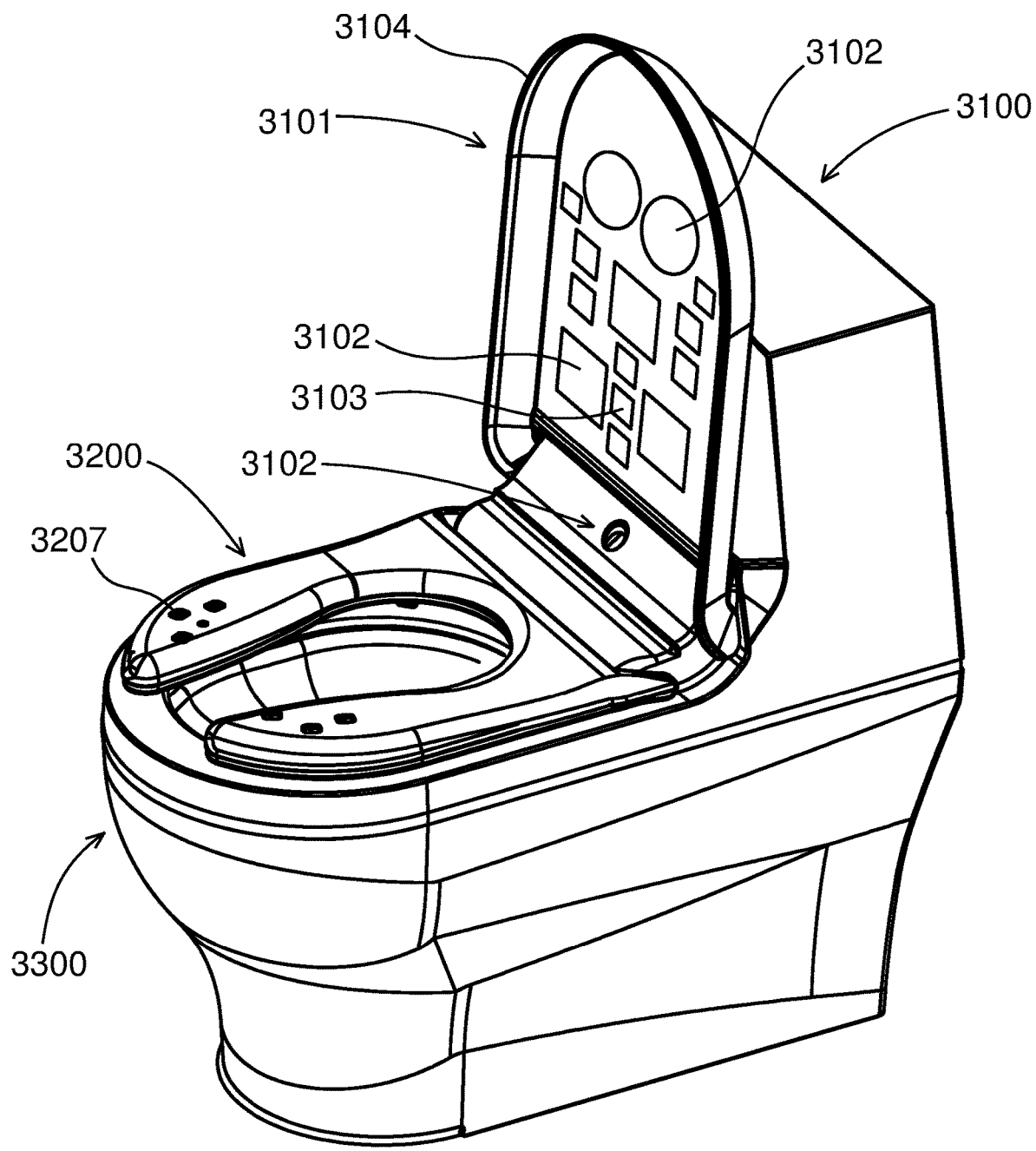
FIG. 16 is a perspective view of an exemplary embodiment of a toilet with a lid and seat having health and wellness sensors according to the present disclosure.
Figure 17:
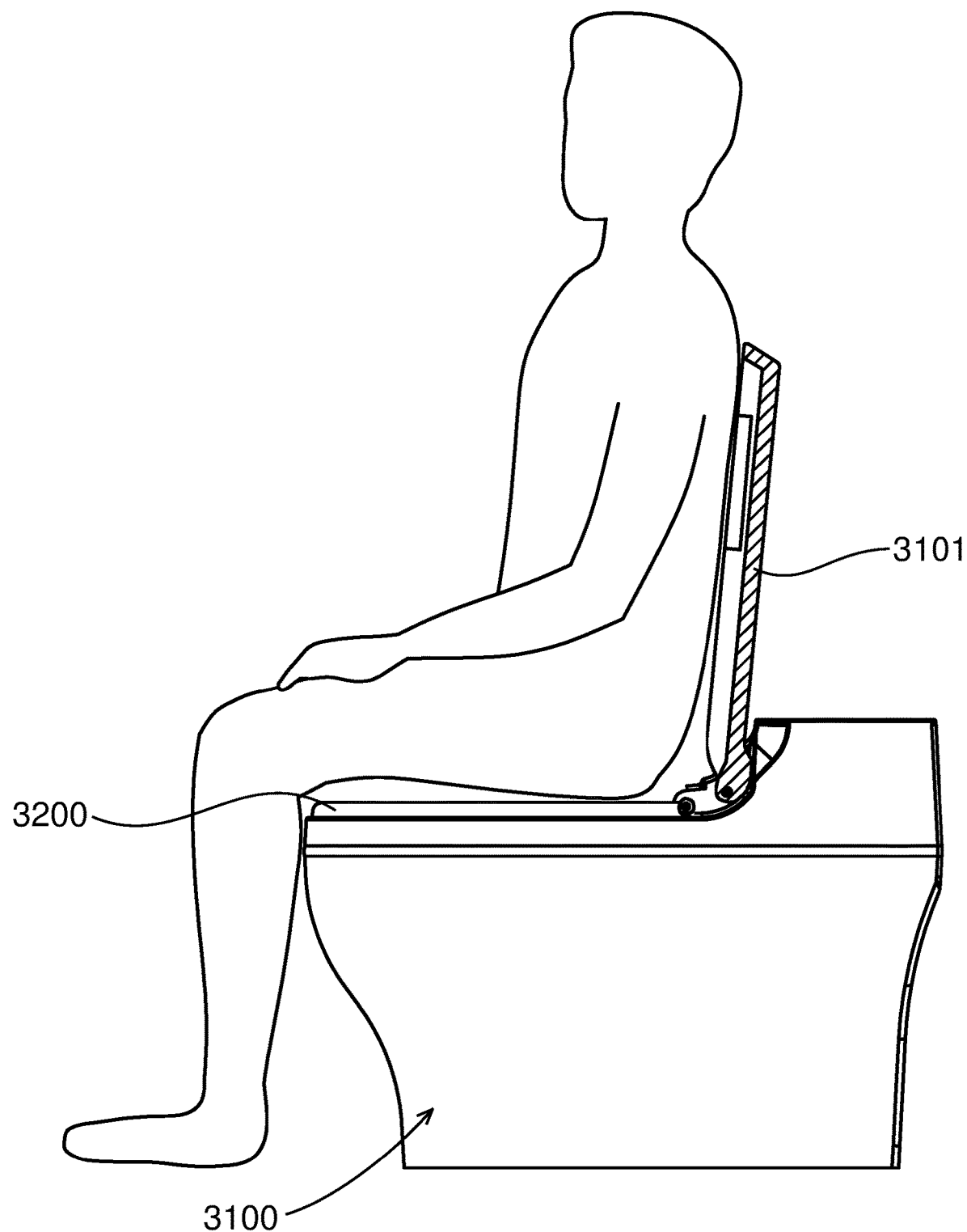
FIG. 17 is a side view of a user sitting on the toilet of FIG. 16.

Referring to FIG. 16, an exemplary embodiment of an analytical toilet 3100 is shown. The seat 3200 includes one or more health and wellness sensors 3207. The lid 3101 includes one or more sensors 3102. The sensors 3102 may interact with the user's back while using the toilet, as shown in FIG. 17, or may be collecting data with the lid 3101 closed. The interior of the bowl 3300 may be illuminated with visual, infrared, near infrared, ultraviolet, or other wavelengths by light sources 3103.

In various exemplary embodiments, the lid 3101 includes a seal 3104 that forms an airtight seal creating an airtight chamber including the bowl 3300. In such embodiments, the toilet may include sensors for testing the air in the chamber and/or passages for drawing air out of the chamber for testing elsewhere in the system. Such sensors or tests may include electrocardiography, CCD, MOS/CMOS, spectrometers, chromatographs, FET, nanoFET, MOSFET, mass spectrometers, electrodes, microphones, load cells, pressure gauges, PPG, thermometers (including IR and thermocouples), rheometers, durometers, pH detectors, and scent detectors.

Figure 18:
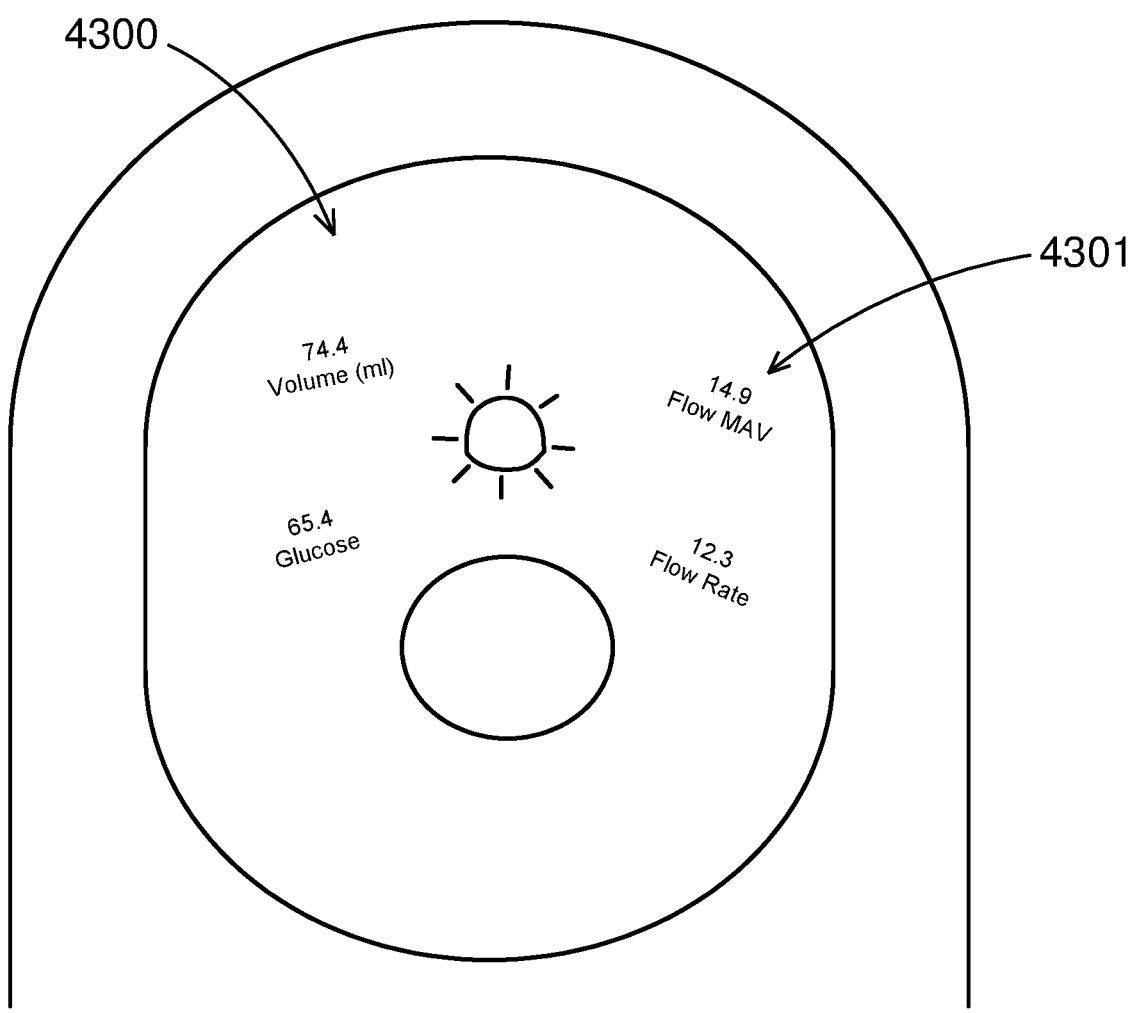
FIG. 18 is a top plan view of a toilet bowl with a visual display according to the present disclosure.

Referring to FIG. 18, an exemplary embodiment of a toilet bowl 4300 that includes a visual display 4301 is shown. The display 4301 may include health and wellness data, health and wellness trend indicators, images, and combinations thereof. Data and trends may include alphanumeric information and color-coded information (e.g., red for negative trends and green for positive trends). The display 4301 may include images for conveying information or for children (e.g., potty training).

In various exemplary embodiments, urine and feces are separated into different collection basins for independent weighing and/or other analysis. In various exemplary embodiments, cameras estimate the volume of the fecal matter and use the estimated volume to estimate density.

In various exemplary embodiments, the toilet is capable of determining the total weight of excreta and the separate weights of solids and liquids. For example, weight may be measured after completion of an excreta event. Liquids may be allowed to exit the bowl and a new weight measurement taken of the remaining solids. The difference in weight provides the weight of liquid excreta. Alternatively, the urine may be drained off at a known flow rate or through a flow meter to measure urine volume leaving only solids to be weighed.

In various exemplary embodiments, a default position for the bowl and/or seat may be selected by the user. In such embodiments, the system will return to this position after being used by someone with a different preferred or optimal position. In various exemplary embodiments, the smart toilet may be programmed with separate default configurations for children and adults.

Preferably, the actuators are controlled by a digital controller that coordinates the actions of the actuators to thereby provide a smooth lifting and lower at the desired speed. More preferably, the controller is programmable, so that users can program the lifting and lowering of the seat to their preference. Even more preferably, the toilet includes a user identification module, so that the user is automatically identified as he or she approaches or sits on the toilet.

In accordance with the present disclosure, a smart toilet that includes mechanical, hydraulic, power, and data connections to accommodate a combination of health measuring tools is provided. An electrical connection to provide power to the health measuring tools is also provided.

In various exemplary embodiments, the smart toilet includes at least one sensor that analyzes imaging data. A processor analyzes the data to attempt to compare the user to known users for identification purposes. If a known user is identified, the position of the bowl and/or seat is automatically adjusted to the preferred position of the user. If the user is unknown or does not have a record preferred position, the processor analyzes the physical characteristics of the user (e.g., height, waist height, length of upper and lower legs) and adjusts the position of the bowl and/or seat accordingly. In some embodiments, facial recognition is used to identify users.

In various preferred embodiments, the system may identify a user based on their face, hand, or foot. In various preferred embodiments, the sensor may include a CCD (charge-coupled device) or MOS (metal oxide semiconductor), including CMOS (complementary metal oxide semiconductor). The sensor can be used, with proper calibration such as taking the data at a known distance, to measure the length of major bones. This data can then be used to customize the toiler position for an unknown user.

In various exemplary embodiments, the toilet system includes sensors for measuring the user's weight. This includes separate sensors for determining user weight on the seat and user weight on the user's feet. The user's weight that is supported by their feet is preferably measured using a platform adjacent to the toilet on which the user's feet are placed while sitting and while being lowered or raised from the toilet.

In the preferred embodiments, the toilet also includes health assessment devices supported by the frame. Examples of such devices include imaging cameras, flow spectrometers, volume measurement devices, body weight sensors, and gas analyzers. Toilets with such devices are described in the patents and published applications cited in the Background section above.

In various exemplary embodiments, the seat and bowl may be lifted together such that the toilet may be used as a urinal. In such a configuration, the system may be designed to flush with a reduced volume of water.

All patents, published patent applications, and other publications referred to herein are incorporated herein by reference. The invention has been described with reference to various specific and preferred embodiments and techniques. Nevertheless, it is understood that many variations and modifications may be made while remaining within the spirit and scope of the invention.

What is claimed is:

1. An analytical toilet comprising:
    a bowl for receiving excreta comprising:
        a fecal portion for receiving feces;
        a feces outlet from the bowl; and
        a urine portion for receiving urine; and
        a urine outlet from the bowl;
            wherein the fecal portion and urine portion are separated by a raised hump;
        at least one bowl load cell for detecting the weight of anything added to the bowl;
        a urine drain comprising a sloped region leading from the raised hump to the urine outlet;
        a urine receptacle below the urine outlet wherein the urine receptacle has a greater vertical dimension than a horizontal dimension; and
        a plurality of urine sensors for detecting at least one property of the urine related to user health and wellness positioned to take measurements at different parts of the receptacle.

2. The analytical toilet of claim 1 further comprising a seat supported by at least one seat weight sensor.

3. The analytical toilet of claim 1 further comprising a non-weight bearing S-seal on both the feces outlet and the urine outlet.

4. The analytical toilet of claim 1 wherein the at least one property of the urine comprises at least one of volume, flow rate, color, weight, density, content, temperature, clarity, pH, settled gradient, and flow geometry.

5. The analytical toilet of claim 1 wherein the plurality of urine sensors comprises at least one of CCD, MOS, CMOS, spectrometers, chromatographs, FET, nanoFET, MOSFET, mass spectrometers, electrodes, microphones, load cells, pressure gauges, PPG, thermometers, rheometers, durometers, pH detectors, and scent detectors.

6. The analytical toilet of claim 1 further comprising at least one health and wellness sensor for detecting health and wellness data about the user.

7. The analytical toilet of claim 6 wherein the at least one health and wellness sensor comprise at least one of electrocardiography, CCD, MOS, CMOS, spectrometers, chromatographs, FET, nanoFET, MOSFET, mass spectrometers, electrodes, microphones, load cells, pressure gauges, PPG, thermometers, rheometers, durometers, pH detectors, and scent detectors.

8. The analytical toilet of claim 6 wherein the at least one health and wellness sensor is located in at least one of a toilet seat, a toilet lid, and a foot platform.

9. The analytical toilet of claim 1 wherein the fecal portion further comprises:
    a platform for feces; and
    water nozzles positioned to release high pressure water onto the platform sufficient to move feces into the feces outlet and clean the platform.

10. The analytical toilet of claim 1 further comprising a feces receptacle below the feces outlet.

11. The analytical toilet of claim 10 further comprising at least one fecal sensor detecting at least one property of the feces in the-fecal receptacle.

12. The analytical toilet of claim 11 wherein the at least one property of the feces comprises at least one of weight, color, consistency, volume, density, content, temperature, pH, size and shape, excretion profile, sounds, and gas or fumes.

13. The analytical toilet of claim 11 wherein the at least one fecal sensor comprises at least one of CCD, MOS, CMOS, spectrometers, chromatographs, FET, nanoFET, MOSFET, mass spectrometers, electrodes, microphones, load cells, pressure gauges, PPG, thermometers, rheometers, durometers, pH detectors, and scent detectors.

14. The analytical toilet of claim 11 wherein the at least one fecal sensor comprises one or more of electrocardiography, CCD, MOS, CMOS, spectrometers, chromatographs, FET, nanoFET, MOSFET, mass spectrometers, electrodes, microphones, load cells, pressure gauges, PPG, thermometers, rheometers, durometers, pH detectors, and scent detectors.

15. The analytical toilet of claim 1 further comprising at least one urine sensor in the bowl for detecting at least one property of the urine.

16. The analytical toilet of claim 15 wherein the at least one urine sensor comprises one or more of electrocardiography, CCD, MOS, CMOS, spectrometers, chromatographs, FET, nanoFET, MOSFET, mass spectrometers, electrodes, microphones, load cells, pressure gauges, PPG, thermometers, rheometers, durometers, pH detectors, and scent detectors.

* * * * *